(12) United States Patent
Novejarque Conde et al.

(10) Patent No.: US 10,736,862 B2
(45) Date of Patent: Aug. 11, 2020

(54) METHOD FOR PRODUCING EXTRACTS CONTAINING HYDROXYCINNAMIC COMPOUNDS FROM VEGETABLE WASTE PRODUCTS

(71) Applicant: HIDROXICINAMICS, S.L., Teulada, Alicante (ES)

(72) Inventors: José Antonio Novejarque Conde, Teulada (ES); José Vicente Pons Raga, Teulada (ES)

(73) Assignee: HIDROXICINAMICS, S.L., Teulada, Alicante (ES)

( * ) Notice: Subject to any disclaimer, the term of this patent is extended or adjusted under 35 U.S.C. 154(b) by 0 days.

(21) Appl. No.: 16/066,931

(22) PCT Filed: Dec. 28, 2016

(86) PCT No.: PCT/ES2016/070941
§ 371 (c)(1),
(2) Date: Jun. 28, 2018

(87) PCT Pub. No.: WO2017/114992
PCT Pub. Date: Jul. 6, 2017

(65) Prior Publication Data
US 2019/0000787 A1    Jan. 3, 2019

(30) Foreign Application Priority Data

Dec. 31, 2015 (ES) .................. 201531951

(51) Int. Cl.
| | | |
|---|---|---|
| *A61K 36/00* | (2006.01) |
| *A61K 31/192* | (2006.01) |
| *A61K 36/28* | (2006.01) |
| *A23L 33/105* | (2016.01) |
| *A61K 36/185* | (2006.01) |
| *A61K 36/81* | (2006.01) |
| *A61K 8/97* | (2017.01) |
| *A61K 36/74* | (2006.01) |
| *A61K 36/22* | (2006.01) |
| *A23L 19/00* | (2016.01) |
| *A23P 10/40* | (2016.01) |
| *A61K 8/9789* | (2017.01) |
| *A23F 5/40* | (2006.01) |
| *A23L 2/52* | (2006.01) |
| *A61K 8/365* | (2006.01) |
| *A61Q 19/08* | (2006.01) |
| *A61Q 19/10* | (2006.01) |

(52) U.S. Cl.
CPC ............ *A61K 31/192* (2013.01); *A23F 5/40* (2013.01); *A23L 2/52* (2013.01); *A23L 19/07* (2016.08); *A23L 33/105* (2016.08); *A23P 10/40* (2016.08); *A61K 8/365* (2013.01); *A61K 8/97* (2013.01); *A61K 8/9789* (2017.08); *A61K 36/185* (2013.01); *A61K 36/22* (2013.01); *A61K 36/28* (2013.01); *A61K 36/74* (2013.01); *A61K 36/81* (2013.01); *A61Q 19/08* (2013.01); *A61Q 19/10* (2013.01); *A23V 2002/00* (2013.01); *A61K 2236/15* (2013.01); *A61K 2236/17* (2013.01); *A61K 2236/331* (2013.01); *A61K 2236/333* (2013.01); *A61K 2236/39* (2013.01)

(58) Field of Classification Search
CPC ...................................................... A61K 36/00
See application file for complete search history.

(56) References Cited

U.S. PATENT DOCUMENTS

| | | | |
|---|---|---|---|
| 8,309,150 | B2 | 11/2012 | Fukuda et al. |
| 9,635,877 | B2 | 5/2017 | Velez et al. |
| 9,688,712 | B2 | 6/2017 | Yamada et al. |
| 2002/0012708 | A1 | 1/2002 | Ruepp |
| 2004/0097584 | A1 | 5/2004 | Graus et al. |
| 2004/0234674 | A1 | 11/2004 | Eich et al. |
| 2011/0237533 | A1 | 9/2011 | Nomura et al. |

FOREIGN PATENT DOCUMENTS

| | | | |
|---|---|---|---|
| CN | 1634853 | A | 7/2005 |
| CN | 1634853 | A | 7/2005 |
| CN | 101811958 | A * | 8/2010 |
| CN | 103204765 | A | 7/2013 |
| CN | 103520228 | A | 1/2014 |
| CN | 104418741 | A | 3/2015 |

(Continued)

OTHER PUBLICATIONS

Llorach et al, Artichoke (*Cynara scolymus* L.) byproducts as a potential source of health-promoting antioxidant phenolics. Journal of agricultural and food chemistry, (Jun. 5, 2002) vol. 50, No. 12, pp. 3458-3464 (Year: 2002).*

(Continued)

*Primary Examiner* — Qiuwen Mi
(74) *Attorney, Agent, or Firm* — Harness, Dickey & Pierce, P.L.C.

(57) ABSTRACT

The invention relates to a method for producing an extract containing hydroxycinnamic acids, characterised in that the method uses one or more vegetable waste products from the production of vegetable food products as a raw material, and comprising the following steps: a) selecting at least one waste product from at least one specific vegetable; b) extracting the hydroxycinnamic acids present in the waste product; c) separating the main liquid phase containing the extracted compounds from the solids; d) clarifying the liquid phase produced in step c); and e) concentrating the clarified liquid phase. The invention also relates to the extract produced via this production method, and the formulations containing this extract.

16 Claims, No Drawings

(56) References Cited

FOREIGN PATENT DOCUMENTS

| WO | WO-9801143 A1 | 1/1998 |
| WO | WO-2006093114 A1 | 9/2006 |
| WO | WO-2008105023 A1 | 9/2008 |
| WO | WO-2011155505 A1 | 12/2011 |
| WO | WO-2013088203 A1 | 6/2013 |
| WO | WO-2014083032 A1 | 6/2014 |

OTHER PUBLICATIONS

Barcia et al, Occurrence of low molecular weight phenolics in *Vitis vinifera* red grape cultivars and their winemaking by-products from Sao Paulo (Brazil). Food Research International (2014), vol. 62, pp. 500-513 (Year: 2014).*

Torres-Mancera, M. T. et al.: "Enzymatic Extraction of Hydroxycinnamic Acids from Coffee Pulp", Food Technol. Biotechnology, 2011, vol. 49, No. 3, pp. 369-373, ISSN 1330-9862.

Garcia-Salas, P., et al.: Phenolic-Compound-Extraction Systems for Fruit and Vegetable Samples, Molecules, 2010, vol. 15, No. 12, pp. 8813-8826; ISSN 1420-3049, Doi:10.3390/molecules15128813.

Gaafar, A. A. et al.: "Phenolic Compounds from Artichoke (*Cynara scolymus* L.) Byproducts and their Antimicrobial Activities", Journal of Biology, Agriculture and Healthcare, vol. 3, No. 12, 2013, pp. 1-7, ISSN 2224-3208 (Paper) ISSN 2225-093X (Online).

Usman, A. et al.: "Effect of Soxhlet and Ultrasound Assisted Extraction on Antioxidant Activity of Pomegranate Peel Extract", International Journal of Food and Nutritional Sciences (IJFNS), vol. 3, Issue 6, Oct.-Dec. 2014, e-ISSN: 2320-7876.

Sumaya-Martinez, T., et al.: "Red De Valor Del Mango Y Sus Desechos Con Base En Las Propiedades Nutricionales Y Functionales", Revista Mexicana De Agronegocios, Quinta Època, Año XVI, vol. 30, Enero-junio del 2012.

International Search Report and Written Opinion issued in PCT/ES2016/070941, dated Mar. 7, 2017; ISA/Oficina Espanola De Patentes y Marcas.

* cited by examiner

METHOD FOR PRODUCING EXTRACTS CONTAINING HYDROXYCINNAMIC COMPOUNDS FROM VEGETABLE WASTE PRODUCTS

CROSS REFERENCE TO RELATED APPLICATIONS

This application is a U.S. National Phase Application under 35 U.S.C. 371 of International Application No. PCT/ES2016/070941 filed on Dec. 28, 2016 and published in Spanish as WO 2017/114992 A1 on Jul. 6, 2017. This application claims priority to Spanish Application No. P201531951 filed on Dec. 31, 2015. The entire disclosures of all of the above applications are incorporated herein by reference.

TECHNICAL FIELD

The present patent application describes a method for obtaining extracts comprising hydroxycinnamic acids such as ferulic, caffeic, p-coumaric or chlorogenic acid, from waste products generated in the commercial upgrading of various plant species, in particular plants of high economic value, thus giving added value to these waste products and obtaining products with reduced production costs.

In addition, the present patent application relates to the use of the extracts obtained, alone or in combination, in food, cosmetic or pharmaceutical applications.

PRIOR ART

The industrial revolution and the improvement in processes achieved throughout the XXth century and to the present time has been reflected in the food industry in a great improvement in food conservation and the prolongation of the shelf life thereof, thus ensuring better and greater availability of foods and thus higher quality of life for a large percentage of the population, particularly in the western world.

In parallel, in the field of cosmetics and pharmaceuticals, with the empowerment of industry and the development of the synthesis of compounds in order to afford higher supply capacity and to reach a larger number of people, products derived from plants fell into neglect.

By means of the purification of foods, heat treatments and the addition of additives obtained predominantly via synthesis, better food conservation was obtained. However, the application of these processes also had negative consequences, in particular the loss of minor components whose biological function was disregarded or undervalued, the food industry focusing only on the macroconstituents, i.e. fats, proteins and carbohydrates. Moreover, far beyond the development of new molecules, the pharmaceutical and cosmetic industries developed molecules derived from already-known molecules, modified for the purpose of potentiating the effects thereof. However, compounds derived from natural sources were not considered because, among other reasons, they were expensive.

The plant sector is characterized by being permanently exposed to the environment, and thus subject to the inclemency thereof, to the action and effects of solar radiation, to attack by environmental changes, such as droughts, sunshine, attack by pathogens, insects and predators, etc. Given their nature, the flight of plants to other areas is unviable, their survival being dependent on their capacity to provide or generate protective components which enable them to withstand such circumstances. Virtually all plant species therefore possess compounds or families of compounds with protective properties. Recent studies have demonstrated that these compounds, which are currently known by the generic term "phytochemicals", although not being essential nutrients, are still useful to human beings.

The list of phytochemical compounds is very extensive, and, among them, the following groups are worth highlighting: terpenoids (isoprenoids), phenolic compounds, glucosinolates, betalains, chlorophylls, other organic acids and protease inhibitors. Among the phenolic compounds that may be encountered are natural monophenols, polyphenols or aromatic acids.

The presence of phytochemical compounds in foods depends on the state of conservation and on the treatment to which said foods have been subjected.

Moreover, a feature of modern society is that it has acquired unhealthy and un equilabrated dietary habits, this being an important factor in the development of medical conditions such as obesity, diabetes, hypertension, cardiovascular problems, ictal phenomena, and various types of cancer. Various epidemiological and biochemical studies have demonstrated that regular ingestion of natural foods is associated with an improvement in these afflictions or medical conditions, such as afflictions related to aging. The protection afforded by fruit and vegetables has been attributed to the presence of antioxidant vitamins (groups C, E and provitamins A), although the latest studies indicate that the compounds responsible for these actions are phenolic compounds, which are very prevalent in plant compounds. (Garcia-Salas, Patricia et al., "Phenolic-Compound-Extraction Systems for Fruit and Vegetable Samples", Molecules 2010, 15, 8813-8826).

These phenolic compounds are widely distributed in plants and contribute to the organoleptic and nutritive quality of fruit and vegetables. In particular, they contribute to the color, taste, aroma and odor thereof and are responsible for the astringency and bitterness thereof. The degree of maturity and the exposure to light of fruit and vegetables have an effect on the content of phenolic compounds and thus on the quality and effects that they produce. The chemistry of phenolic compounds is very complex, given their high capacity for reacting with other compounds and themselves, and as such they constitute a highly complex group with strong synergistic actions, such that the effects detected is generally due to the combination of phenolic compounds present in a product. As a result of these features, these phenolic compounds are collectively termed "polyphenolic compounds".

The term "polyphenol" includes more than 8000 compounds with great structural diversity, but which at least have in common an aromatic ring with one or more hydroxyl groups. Polyphenols may be divided into various classes depending on their basic structure; the main families are indicated in the following table:

| Number of carbons | Basic structure | Class |
|---|---|---|
| $C_6$ | phenol (–OH) | Simple phenols |
| | benzoquinone (O=⬡=O) | Benzoquinones |
| $C_6$—$C_1$ | benzoic acid (–COOH) | Benzoic acid |
| $C_6$—$C_2$ | acetophenone (–CO–CH₃) | Acetophenones |
| | phenylacetic acid (–CH₂–COOH) | Phenylacetic acid |
| $C_6$—$C_3$ | cinnamic acid (–CH=CH–COOH) | Cinnamic acid |
| | phenylpropene (–CH=CH–CH₂) | Phenylpropene |
| | coumarin | Coumarins |
| | chromone | Chromones |
| $C_6$—$C_4$ | naphthoquinone | Naphthoquinones |
| $C_6$—$C_1$—$C_6$ | xanthone | Xanthones |
| $C_6$—$C_2$—$C_6$ | stilbene | Stilbenes |

| Number of carbons | Basic structure | Class |
| --- | --- | --- |
| | (anthraquinone structure) | Anthraquinones |
| $C_6-C_3-C_6$ | (flavonoid structure) | Flavonoids |
| $C_6-C_4-C_6$ | (lignan structure) | Lignans, neolignans |
| $(C_6-C_1)_n$ | Heterogeneous polymers composed of phenolic acids and simple sugars | Hydrolyzable Tannins |
| $(C_6-C_2)_n$ | Highly crosslinked aromatic polymers | Lignins |

Anti-carcinogenic, anti-inflammatory, antibacterial and enzyme-activity-regulating properties and powerful antioxidant properties have been attributed to polyphenolic compounds.

Among polyphenolic acids, two main groups are worth highlighting: benzoic acid derivatives (C6-C1) and cinnamic acid derivatives (C6-C3). These compounds appear predominantly, respectively, as hydroxybenzoic acids and hydroxycinnamic acids, both in free and conjugated form.

Hydroxycinnamic acids are considered to be structural and functional constituents of the cell walls of plants. In addition, they are bioactive ingredients of food. Recent studies have revealed their effects as preventive or therapeutic agents in certain medical conditions related to oxidative stress, such as arteriosclerosis, inflammation or cancer, and also their substantial cardioprotective, anti-obesity and antidiabetic effects. In addition, hydroxycinnamic acids have very positive synergistic effects in many modern medical conditions. Furthermore, various studies have shown the dependency between the antioxidant capacity of hydroxycinnamic acids and the position of the hydroxyl groups in the structure; in particular, the presence of hydroxyl groups in the aromatic structure of these compounds gives rise to higher antioxidant capacity.

The hydroxycinnamic acid family is very broad, and may be divided into four main subgroups: aglycones, esters, oligomeric forms and forms conjugated with coenzyme A.

In turn, aglycones may be selected from the group consisting of cinnamic acid (the precursor of this family), monohydroxycinnamic acids such as p-coumaric acid, o-coumaric acid and m-coumaric acid; dihydroxycinnamic acids such as caffeic acid (3,4-dihydroxycinnamic acid), umbellic acid (2,4-dihydroxycinnamic acid), 2,3-dihydroxycinnamic acid, 2,5-dihydroxycinnamic acid and 3,5-dihydroxycinnamic acid; trihydroxycinnamic acids such as 3,4,5-trihydroxycinnamic acid and 3,4,6-trihydroxycinnamic acid; O-methyl forms such as ferulic acid, 5-hydroxyferulic acid and sinapinic acid; and others such as plicatin A and plicatin B.

Moreover, the subgroup of esters may be selected from the group consisting of esters of glucoside type, tartaric acid esters, other caffeic acid esters and caffeoyl phenylethanoid glucosides (GPG). In turn, the esters of glucoside type may be selected from the group consisting of esters of caffeic acid with cyclitols and glucosides. More specifically, the esters of caffeic acid with cyclitols may be selected from the group consisting of quinic acid esters such as chlorogenic acid (3-caffeoylquinic acid), cryptochlorogenic acid (4-O-caffeoylquinic acid), neochlorogenic acid (5-O-caffeoylquinic acid), cyanarin (1,5-dicaffeoylquinic acid), 3,4-dicaffeoylquinic acid and 3,5-dicaffeoylquinic acid; and shikimic acid esters such as dactylifric acid (3-O-caffeoylshikimic acid). Moreover, the glucosides may be selected from the group consisting of ferulic acid glucoside, p-coumaric acid glucoside and 1-sinapoyl-D-glucose.

The tartaric acid esters may be selected from the group consisting of caftaric acid, chicoric acid (dicaffeoyltartaric acid), coutaric acid, fertaric acid and caftaric acid conjugated with glutathione (reaction product of grape). The other caffeic acid esters may be selected from the group consisting of caffeoylmalic acid, ethyl caffeate, methyl caffeate, caffeic acid phenethyl ester (CAPE) and rosmarinic acid (ester of lactic acid with 3,4-dihydroxyphenol).

The caffeoyl phenylethanoid glucosides (CPG) may be selected from the group consisting of echinacoside, calceolarioside A, B, C and F, chiritoside A, B and C, cistanoside A, B, C, D, E, F, G and H, conandroside, myconoside, pauoifloside, plantainoside A, plantamajoside, tubuloside B, verbascoside such as isoverbascoside and 2'-acetyleverbascoside.

The hydroxycinnamic acids included in the subgroup of the oligomeric forms may be selected from the group consisting of dimers, in particular diferulic acids (DIFA) such as 5,5'-diferulic acid, 8-O-4'-diferulic acid, 8,5'-diferulic acid, 8,5'-DIFA (DC), 8,5'-DIFA (BF) and 8,8'-diferulic acid; trimers, in particular triferulic acids such as 5,5',8'-O-4"-triferulic acid; and tetramers such as tetraferulic acids.

Finally, the forms conjugated with coenzyme A may be selected from the group consisting of caffeoyl-coenzyme A, cinnamoyl-coenzyme A and coumaryl-coenzyme A.

Among the hydroxycinnamic acids mentioned previously, the most important and significant are caffeic, chlorogenic, ferulic, sinapinic and p-coumaric acids; their chemical structures are presented hereinbelow. The presence and concentration of these compounds is used as a studied therapeutic or biological action indicator, although the effects are generally due to the synergistic action of these compounds and other hydroxycinnamic derivatives that are usually present in smaller amount.

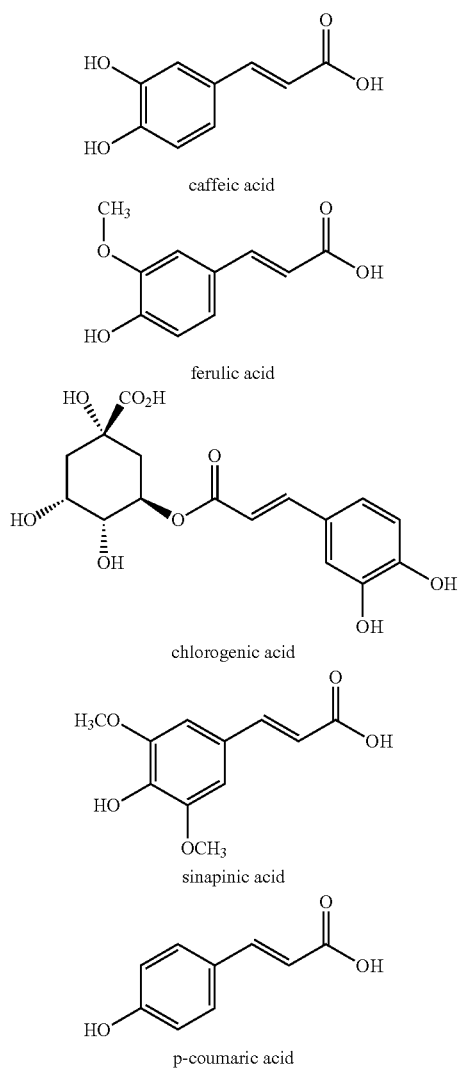

caffeic acid ferulic acid chlorogenic acid sinapinic acid p-coumaric acid

As a result of all the properties indicated, renewed interest has been shown in hydroxycinnamic acids in dietetic and nutritional applications in the functional food sector, in the pharmaceutical sector due to their therapeutic effects, and in the cosmetics industry as a result of their antioxidant properties and as UV stabilizers.

As mentioned previously, hydroxycinnamic acids are very widely distributed in plants. However, they are present in very low proportions relative to the total mass of the plant, and as such only regular and substantial consumption of products rich in these compounds can ensure an adequate intake to achieve the desired protective effects.

Many of the widespread food production crops are species which contain, in addition to the intrinsic nutritional elements, relatively high levels of polyphenolic compounds. The majority of the food products of this type are subjected to industrial transformations, for the purpose of improving their average shelf life and of facilitating distribution to a wider segment of the population.

The beneficial effects of the polyphenolic compounds which they contain require the regular and substantial consumption of large amounts of the product, since the doses required to obtain said effect are otherwise not reached. Thus, this is why it is increasingly common to reinforce processed products with selective ingredients which make it possible to reach the required doses more easily; alternatively, other products with the same effects which supplement the diet are incorporated therein.

However, obtaining polyphenolic compounds such as hydroxycinnamic acids for the enrichment of other compositions is an expensive process given the low availability of plant materials that are suitable to be extracted effectively, and also the high cost of the harvested product, given its higher profitability as a staple food.

Industrialization of the production of foods of plant origin is focused on the handling, conservation and preparation of the plant part that is liable to be consumed, and consequently large amounts of waste products are generated, which are frequently a cause of environmental problems and the utilization of which is complicated and relatively inefficient. Depending on the species under consideration, the amounts of waste products that are generated may range from 25% to 85% (M. T. Torres-Mancera et al. "Enzymatic Extraction of hydroxycinnamic acids from Coffee Pulp", Food Technol, Biotechnol. (2011) 49 (3) 369-373; Gaafar, A. A. et al., Phenolic Compounds from Artichoke (*Cynara scolymus* L.) Byproducts and their Antimicrobial Activities, Journal of Biology, Agriculture and Healthcare, Vol. 3, No. 12, 2013, 1-7; Usman A. et al., "Effect of Soxhlet and ultrasound assisted extraction on antioxidant activity of pomegranate peel extract", International Journal of Food and Nutritional Sciences (IJFNS), Vol. 3, Iss. 6, October-December 2014; Sumaya-Martinez, Ma. T. et al. "Red de Valor del Mango y sus desechos con base en las propiedades Nutricionales y funcionales [Value network for mango and waste products thereof based on the nutritional and functional properties]". Revista Mexicana de Agronegocios. Fifth season. Year XVI. Volume 30. January-June 2012), thus being very large volumes.

In the industrialization of a product of plant origin, the highest costs correspond to the economic upgrading of the raw material in the field, but the costs associated with collecting, grading, transporting and handling these foods are ever-increasing. In the method described in the present patent application, the raw material used is waste material generated during the preparation and handling of the food product of plant origin. In this way, the main cost factors are absorbed by the food product that is to be processed, i.e. the harvested fruit or vegetable, and the costs associated with the work involved in collecting and concentrating the waste plant mass, which is the raw material of the method of the present invention, remain reduced to the industrial environments in which the food is processed.

Extracts comprising polyphenolic derivatives obtained from plant material are known in the prior art. For example, patent application US 2004/0097584 A1 describes the stimulation of T lynphocytes using one or more plant extracts which contain chlorogenic acid or functional derivatives thereof, mention being made of plants of *Echinacea* origin, ginseng, green coffee, green cocoa, hawthorn, green tea, artichoke, elderberry, arnica, *Phoenix* spp., *Butia capitata*, dandelion, mixtures of dicots and birch. However, said patent application starts with the whole plant and does not describe any specific extraction or concentration process.

Moreover, patent application US 2011/0237533 A1 describes the production of a novel polyphenolic complex which inhibits lipase activity, and also the use thereof in food and pharmaceutical preparations, but the production of said complexes is performed by the combination/reaction of a flavonoid-rich natural compound with other compounds rich in caffeic, gallic or chlorogenic acid derivatives, and/or catechin derivatives by reacting with polyphenol oxidase.

Patent application WO 98/01143 establishes novel uses of artichoke extracts combined with other *Echinacea* derivatives for the treatment of medical conditions or as palliatives for other treatments or coadjuvants in other aggressive treatments. However, said patent application does not specify the source, i.e. the part of the artichoke plant that is used as starting material, nor the method for obtaining the extracts.

Patent application WO 2008/105023 (EP 2 131 681 B1) describes a process for obtaining purified extracts from waste material from the industrialization of artichoke.

In addition, said patent application describes the use of the extract obtained in food and also in cosmetics and pharmaceuticals.

Moreover, patent application WO 2013/088203 A1 describes the production of a concentrate obtained from the washing waters generated from the wet milling of coffee cherries, rich in sugars, and for the purpose of obtaining a sweetened syrup with certain antioxidant properties. Said patent application focuses on the factors for using waste products as a means of reducing the environmental cost via the recycling of solids as compost.

WO 2014/083032 A1 establishes a process for obtaining pectin from green coffee cherries by extraction and enzymatic treatment.

Various patents WO 2006/093114 A1 and WO 2011/155505 A1, from 2006 and 2011, respectively, relate to the production of caffeine-free chlorogenic acid preparations from green or roasted coffee beans.

CN 103520228 A published in 2014 relates to the use of raw mango extracts as a base for the preparation of medicaments with cardiovascular activity.

Finally, patent CN 1634853 A from 2005 relates to establishing the waste product from tobacco production as an alternative source for obtaining chlorogenic acid by extraction thereof from the waste material and subsequent purification to obtain the purified product via ultrasonic and microwave techniques and selective solvents.

Patent CN 103204765 A1 relates to simultaneously obtaining solanesol and chlorogenic acid by aqueous-alcoholic extraction followed by filtration through ceramic membranes, selective redissolutions and the use of column chromatography.

DESCRIPTION

In a first aspect, the present patent application relates to a method for obtaining an extract which comprises hydroxycinnamic acids, characterized in that the method uses as starting material one or more plant waste products from the production of plant-based food products, and comprises:
a) selecting at least one waste product from at least one plant species,
b) extracting the hydroxycinnamic acids present in the waste product via a technique selected from the group consisting of washing, decoction, maceration, percolation and any combination thereof,
c) separating the main liquid phase which comprises the extracted compounds from the solids greater than 2 mm in size,
d) clarifying the liquid phase obtained in step c), and
e) concentrating the clarified liquid phase.

The method described in the present invention makes it possible to obtain an extract which comprises hydroxycinnamic acids. In particular, the method of the present invention makes it possible to obtain an extract with an enrichment of at least five-fold relative to the concentration of hydroxycinnamic acids present in the waste product used as starting material, in which the proportion of the various hydroxycinnamic acids will depend to a large extent on the plant species used as starting material.

Thus, the method for obtaining an extract comprising hydroxycinnamic acids which is described in the present patent application uses as starting material a waste product from the industrial processing or use of plant-based food products such as fruit or vegetables. In particular, the starting materials used may be the skins, leaves, stems, bracts, pulp, coverings, rejects and residues in general from the processing of the plant species under consideration. Generally, the amount of polyphenolic compounds, in particular hydroxycinnamic acids, in these waste materials may vary relative to the food per se, being lower in some cases, whereas in other cases the content of these compounds in the waste material may be equal to or even greater than that in the vegetable, fruit or stalk used as food.

The choice of the starting plant species, or combination of species, is conditioned by the activity of interest in the extract obtained. The activity of the compounds known as hydroxycinnamic acids and derivatives thereof is a continual source of new discoveries, since their antioxidant properties and their biological activity make them very advantageous in a multitude of applications. In particular, in the food sector, these compounds can improve the taste properties of food, for example by acting as flavor enhancers or taste-masking agents; similarly, they may also exert protective functions, for example as antioxidants, free-radical scavengers, etc. Moreover, in the cosmetic and pharmaceutical sectors, hydroxycinnamic acids are advantageous given their capacity to potentiate the immunological system, or to act as anticancer, cardioprotective, antidiabetic, etc. agents.

The therapeutic effects mentioned previously are a consequence of the synergistic activity of the combination of hydroxycinnamic acids, occasionally also in combination with other polyphenolic compounds that are found in a plant. In point of fact, it is occasionally beneficial to obtain a combination of extracts from different plants, given that better results are obtained by combining the action of the various molecules present in each of these extracts. As mentioned previously, it is possible to identify compounds which act as indicators or markers of the concentration of or richness in antioxidant compounds and thus of the expected action, hydroxycinnamic acids being the ones most used for this purpose: chlorogenic acid, caffeic acid, ferulic acid and p-coumaric acid. Among these, the one most used as marker is chlorogenic acid, although chlorogenic acid itself and other compounds with similar functional properties (in general quinic acid esters) are generally grouped under this name.

The plant species that it is preferred to use as starting material in the method of the present invention are those which include hydroxycinnamic acids among their main compounds and, in addition, at least one industrialization process associated with the use of said plant species exists and, as a result, waste products derived from this industrialization process which are concentrated at the point of transformation may be obtained. In this way, the method described in the present patent application makes it possible to obtain an extract which comprises hydroxycinnamic acids at reduced cost, which simultaneously increases the profitability of the process for industrialization of the plant species under consideration and contributes toward eliminating or reducing the environmental impact of said industrialization process, by economically upgrading the waste products obtained in said process.

These waste materials may be skins, leaves, stems, bracts, pulp, coverings, rejects and, in general, any plant waste product obtained during the processing of the plant species.

Consequently, the plant species that are preferred for use in the method for producing an extract comprising hydroxycinnamic acids are artichoke (*Cynara scolymus*), the processing of which generates more than 75% of bract, leaf, receptacle and stem residues; eggplant (*Solanum melongena*) and solanaceae plants in general, since the skin, leaves and stems may be used as starting waste product in the method of the invention; green coffee (*Coffea arabica*) and maqui (*Aristotelia chilensis*), the processing of which gives rise to berries, cherries, pulp and mucilage as waste products that may be used in the method of the present invention; pomegranate (*Punica granatum*) and mango (*Mangifera indica* L.), of which use may be made of the skin, rind and pulp; and tobacco (*Nicotiana tabacum*), since use may be made of the leaves, dust, stalks and waste material obtained in its processing as starting material in the method of the present invention. In addition, use may also be made as starting material of waste products obtained in the industrial processing or use of cranberry, acai, wolfberry, acerola, noni, pear, mangosteen, cabbage, kohlrabi, broccolini, black garlic, yerba mate, celery and plants of the sage group.

For the purpose of ensuring that the plant waste products are suitable for use as starting material in the method of the present invention, they are preferably subjected to a quality control analysis prior to their use. This analysis may comprise the determination of the water activity of the residual material, its state of maturity and conservation, the presence of free degradation esters and the contamination thereof.

The plant waste products which constitute the starting materials of the method of the invention are preferably subjected to a pretreatment prior to step b) to facilitate the extraction process. In particular, these waste products may be partially dried to facilitate their handling, and this may be performed by natural means, i.e. by sun-drying, or artificial drying with a stream of air at a temperature not greater than 75° C., preferably less than 50° C. Preferably, this drying process is performed until the waste product reaches a moisture content of less than 70%, preferably between 40-50% and even more preferably less than 40%, these amounts being expressed as weight percentage of water relative to the total weight of the waste product.

In addition, in order to increase the surface area of contact during the extraction process and, consequently, to improve the efficiency of this process, the pretreatment may comprise chopping the plant waste products to a particle size of less than 10 cm, preferably between 2-4 cm, more preferably less than 20 mm and ideally less than 10 mm.

For waste materials originating from the pulping of berries or cherries, these materials are preferably used directly, or alternatively they are wet-chopped, i.e. chopped in the presence of water, for the purpose of increasing the efficiency of the extraction process.

The extraction of the hydroxycinnamic acids is performed by washing, decoction, maceration and/or percolation of the waste products optionally pretreated as indicated previously. This extraction may be performed with a pure solvent or with a mixture formed from two solvents chosen from the group consisting of water, methanol, ethanol, acetone and ethyl acetate. Preferably, water or a mixture of solvent and water in solvent/water proportions that may range from 20/1 to 1/20, preferably from 10/1 to 1/10 and more preferably from 5/1 to 1/2 is used. The extraction solutions may be neutral, acidic or basic, by adding an amount of between 0 and 5%, preferably between 0 and 2%, of a reagent chosen from the group consisting of hydrochloric acid (HCl), acetic acid (AcOH), caustic soda (sodium hydroxide: NaOH), ammonia ($NH_3$) and potassium hydroxide (KOH), it even being possible to use calcium or sodium carbonate for this same purpose, and the final pH being adjusted to between 3-10.

The temperature of the extraction process may range between 15° C. and 95° C., preferentially between 20° C. and 65° C., the contact times possibly ranging between 15 minutes and 5 hours, preferably between 1 and 2 hours. Optionally, use may be made of MAE (microwave) techniques or, at a higher frequency, UAE (ultrasound) techniques using an ultrasonic frequency of between 20 and 40 kHz, and an intensity of between 10-30 $W/cm^2$, optionally with programmed pulses in cycles of up to 10-6 seconds and contact times of less than 1 hour.

After the extraction process, the solution is subjected to a process of removing the coarse matter in order to separate the main liquid phase comprising the extracted compounds from the solids greater than 2 mm in size; a vibrating screen or a basket centrifuge with a porosity of greater than or equal to 2 mm may be used to perform this separation.

The solids separated out in step c) may be subjected to a second extraction step, preferably under the same conditions as the first step performed in step b) of the method described in the present patent application. Once this second extraction is complete, the secondary liquid phase is separated from the solids greater than 2 mm in size, for which a vibrating screen or a basket centrifuge with a porosity of greater than or equal to 2 mm may again be used, and the secondary liquid phase is mixed with the main fraction obtained previously.

The liquids obtained on conclusion of the coarse matter removal step c) may be cooled to a maximum temperature of 43° C., if necessary, and then subjected to clarification by using, for example, high-efficiency centrifuges, ultracentrifugation or filtration on paper or polymeric or non-polymeric membranes and preferably filtration of tangential type.

The solution thus filtered may be concentrated using vacuum evaporators, which may be simple boilers or, preferably, falling-film or rising-film vacuum evaporation systems, with or without stirring assistance and at temperatures below 70° C., preferably below 45° C.

This concentration step continues until an extract is obtained which comprises hydroxycinnamic acids, preferably as main components, until the concentration required for the final application of the extract is obtained, said concentration preferably ranging from 50% by weight of solids relative to the total weight of the concentrated extract, to dryness. In starting materials comprising a high content of sugars, the final concentration of the extract is preferably established such that it provides a minimum of 66° Brix of sugars.

The extract obtained via the method described in the present patent application may be used directly in liquid form, or may be dried until it forms a powder, for example by means of spray-drying techniques. In this case, it is preferred to add maltodextrins before the drying step to improve the texture and stability of the powder obtained.

In the majority of applications, the quality obtained via the extraction method described in the present patent application is sufficient to allow a broad spectrum of use. However, for certain particular applications, a higher degree of purity or concentration of hydroxycinnamic acids may be required, and in this case the method of the present invention may comprise concentration to dryness of the extract in step e), redissolution of the concentrate obtained in ethyl acetate, subsequent concentration of the hydroxycinnamic acids by means of macroporous chromatographic resins, and elution with ethyl alcohol to a richness of 55-65% and prior adjustment of the pH to 3-3.5 using hydrochloric or acetic acid, which allows more selective extraction, filtration of the solution obtained and crystallization of the components thereof while leaving to stand for 12 hours, until room temperature is reached.

The present invention also relates to extracts comprising hydroxycinnamic acids, preferably in an amount at least five times greater than their concentration in the residue used as starting material. In particular, this extract may comprise as main components one or more hydroxycinnamic acids selected from the group consisting of caffeic acid, chlorogenic acid, ferulic acid, sinapinic acid and p-coumaric acid.

In addition, these extracts may comprise other active principles such as amino acids, vitamins, minerals and phytochemical compounds chosen as a function of the final application of the extract. These active principles may be derived from the plant waste product used as starting material in the method of the invention, or may be added subsequently in any of the steps of the method described in the present patent application.

In addition, the present invention also relates to the use of the extracts obtained via the method described in the present patent application in the food, pharmaceutical or cosmetic industry. In particular, they may be used in the food sector for improving the taste properties of a food, for example by acting as flavor enhancers or taste-masking agents; similarly, they may also exert protective functions on food, for example as antioxidants, free-radical scavengers, etc. Moreover, in the cosmetic and pharmaceutical sectors, the extracts obtained via the method of the present invention may be used to potentiate the immune system, or to act as anticancer, cardioprotective or antidiabetic agents.

The present invention also relates to a formulation, in particular a food, cosmetic or pharmaceutical formulation, which comprises the extract obtained via the method described in the present patent application. This formulation may additionally comprise other active principles, for instance amino acids, vitamins, minerals and phytochemical compounds chosen as a function of the final application of the formulation.

This pharmaceutical formulation may be a product designed for use in orthomolecular medicine, i.e. special products devoted to cellular rehabilitation, which supply the body with essential nutrients. Orthomolecular medicine was founded by the French biologist Louis de Brouwer, a doctor in medicine and molecular biology, international consultant of the UNO and of UNESCO in health and oncology. The orthomolecular foundations are based on the studies of four outstanding scientists: Albert Szent-Gyorgyi, Otto Warburg, Everett Storey and Linus Pauling, who, among them received seven Nobel prizes.

Similarly, the present patent application also relates to the extract obtained via the process described, or to a formulation which comprises said extract, for use in medicine, in particular for use in the treatment or prevention of a medical condition which requires potentiation of the immune system, or for treating or preventing cancer, cardiovascular diseases or diabetes.

These formulations may be obtained by mixing and homogenizing the various ingredients of which they are composed, in installations that are suitable therefor, in particular in white rooms which meet the GMP standards, standard DIN EN ISO 16644-1. In certain embodiments of the present invention, the formulation may be obtained via a supercritical fluid system and process, for obtaining a quality and purity of the final components that meet particular stipulations required for specifics.

The mixing and homogenization of the various ingredients of the formulation may be performed by applying ultrasound, preferably over a time interval of 16 to 60 minutes, at a temperature of between 14 and 33° C.

Once all the ingredients have been mixed and homogenized, quality controls which ensure the product quality are generally performed. Preferably, these controls include: determining the interaction between the components of the formulation (existence of synergism), controlling the pH, redox potential and environmental factors such as light, air, etc.; determining the TROLOX/DPPH/ORAC/FRAF indices, excluding possible interaction of the extract with the container which will contain the formulation.

EXAMPLES

Example 1: Production of an Extract Comprising Hydroxycinnamic Acids from Artichoke Leaves Artichoke basal leaves and gills were selected as starting material to perform this example. Extraction of the hydroxycinnamic acids was performed at 75° C., by recirculation of water. Next, the main liquid phase was separated from the solids greater than 2 mm in size and a second extraction step was performed using the solids separated out, at 75° C. and by recirculation of water. At the end of extraction, the solids greater than 2 mm in size were separated out and the extracted liquid phase was added to the main liquid phase obtained after the first extraction step.

The mixture of extracted liquid phases was then clarified by conventional filtration using a filter press, and the filtrate was concentrated under vacuum until a solution containing 50% w/w of solids was obtained. This concentration step was performed at a maximum temperature of 70° C. and under vacuum (less than 50 mbar). In this manner, an extract with a minimum chlorogenic acid richness of 4.5% was obtained.

For applications requiring a dry product, the concentrated extract obtained in the preceding step may be dried in a vacuum tray oven.

Example 2: Cell-Repairing Bath Gel

Water 54.4%
Surfactants 40%
Thickeners 3%
Preserving agent 0.1%
Fragrance 0.7%
Active principles 0.8%
(*) Extract comprising hydroxycinnamic acids 1%

Example 3: Energizing Antiaging Serum

Water 87.95%
Thickener 1%
Glycerol 3%
Preserving agent 0.05%
Distilled orange blossom water 3%
Active principles 3%
(*) Extract comprising hydroxycinnamic acids 2%

Example 4: Tomato Drink

Tomato juice 95.90%
Lemon juice 1%
Tabasco 0.7%
Celery salt 0.4%
(*) Extract comprising hydroxycinnamic acids 2%

Example 5: Caffeinated and Decaffeinated Soluble Coffee

Dry extract of coffee 98.90% (obtained by atomization or by lyophilization)
Vitamins E and B1 (thiamine) 0.4%
Magnesium 400 mg
(*) Extract comprising hydroxycinnamic acids 0.7%
The caffeinated soluble coffee contains >0.3% and the decaffeinated soluble coffee contains <0.3%, in both cases with a maximum moisture content of 5%.

Example 6: Food Supplement in Capsules

Two plant capsules provide:
Vehicles (plant-based microcrystalline cellulose-magnesium stearate)
Plant-based hydroxypropylmethylcellulose capsule healthful plant extracts and active principles
Plant base powder (extract of boldo, extract of *Ginkgo biloba, spirulina* alga) 60 mg
Plant-based antioxidants/(*) Extract comprising hydroxycinnamic acids 100 mg
Mixture of tocopherols 21 mg
Zinc 7 mg
Riboflavin 5 mg
Copper 1000 micrograms
Selenium 50 micrograms
(*) The extract used in Examples 2 to 6 was obtained by following the method described in Example 1.

The invention claimed is:

1. A method for producing an extract comprising hydroxycinnamic acids, wherein the method uses as raw material one or more plant wastes from the production of plant-based food products, and comprises:
   a) selecting at least one waste product from at least one plant species,
   b) extracting the hydroxycinnamic acids present in the waste by means of a technique selected from the group consisting of washing, decoction, maceration, percolation and a combination of any of the above,
   c) separating the main liquid phase which comprises the compounds extracted from the solids with a size greater than 2 mm,
   d) clarifying the liquid phase obtained in stage c),
   e) concentrating the clarified liquid phase to dryness,
   f) re-dissolving the concentrate of step e) with ethyl acetate, and
   g) concentrating the hydroxycinnamic acid to a richness of 55-66% by means of macroporous chromatographic resin using ethyl alcohol as an elution solvent and adjusting the pH to from 3 to 3.5 with an acid.

2. The method for producing an extract according to claim 1, wherein the plant waste used as raw material comes from the industrial processing or use of plant-based products.

3. The method for producing an extract according to claim 2, wherein the plant waste used as raw material is selected from the group consisting of skins, leaves, stalks, bracts, pulp, packagings and rejected product.

4. The method for producing an extract according to claim 1, wherein the plant waste is one or more species selected from the group consisting of artichoke, aubergine, green coffee, maqui, pomegranate, mango, tobacco and a combination of any of the above.

5. The method for producing an extract according to claim 1, comprising an additional pre-treatment stage of the plant waste before the extraction step b).

6. The method for producing an extract according to claim 5, wherein the pretreatment comprises drying the plant waste to a humidity lower than 70%.

7. The method for producing an extract according to claim 5, wherein the pre-treatment comprises chopping the plant waste to a size smaller than 10 cm.

8. The method for producing an extract according to claim 1, wherein the extraction stage takes place in water or in a water/solvent mixture, wherein the solvent is selected from the group consisting of methanol, ethanol, acetone and ethyl acetate.

9. The method for producing an extract according to claim 1, wherein the extraction stage takes place between 15° C. and 95° C.

10. The method for producing an extract according to claim 1, wherein the solids separated in stage c) are subjected to a second extraction in the same conditions as the extraction carried out in stage b), the secondary liquid phase is separated from the solids with a size greater than 2 mm, and this secondary liquid phase is mixed with the main liquid phase produced previously.

11. The method for producing an extract according to claim 1, comprising an additional stage h) wherein the concentrate from stage g) is transformed into powder by means of a spray-drying technique, wherein maltodextrin is added prior to the drying step.

12. A method for producing a food, cosmetic or pharmaceutical composition, wherein the composition comprises an extract comprising hydroxycinnamic acids, the method comprises:
   a) selecting at least one waste product from at least one plant species,
   b) extracting the hydroxycinnamic acids present in the waste by means of a technique selected from the group consisting of washing, decoction, maceration, percolation and a combination of any of the above, c) separating the main liquid phase which comprises the compounds extracted from the solids with a size greater than 2 mm, d) clarifying the liquid phase obtained in stage c), e) concentrating the clarified liquid phase to dryness, f) re-dissolving the concentrate of step e) with ethyl acetate, g) concentrating the hydroxycinnamic acid to a richness of 55-66% by means of microporous chromatographic resin using ethyl alcohol as an elution solvent and adjusting the pH to from 3 to 3.5 with and acid, and h) mixing and homogenizing the hydroxycinnamic acid extract of step g) with a suitable ingredient.

13. The method for producing for producing a food, cosmetic or pharmaceutical composition according to claim 12, comprising an additional stage between stage g) and f) wherein the concentrate from stage g) is transformed into powder by means of a spray-drying technique, wherein maltodextrin is added prior to the drying step.

14. The method for producing for producing a food, cosmetic or pharmaceutical composition according to claim 12, wherein the composition is cell repairing bath gel, an energizing antiaging serum, a tomato drink, a decaffeinated or caffeinated soluble coffee or a food supplement capsule.

15. The method for producing for producing a food, cosmetic or pharmaceutical composition according to claim 12, wherein the mixing and homogenizing of step h) is performed by applying ultrasound at time intervals between 16 to 60 min.

16. The method for producing for producing a food, cosmetic or pharmaceutical composition according to claim 12, wherein the mixing and homogenizing of step h) is performed at a temperature of between 14 to 33 ° C.

* * * * *